United States Patent [19]

Schneider

[11] Patent Number: 4,626,250
[45] Date of Patent: Dec. 2, 1986

[54] MALE URINARY COLLECTION SYSTEM AND EXTERNAL CATHETER THEREFOR

[75] Inventor: Barry L. Schneider, Deerfield, Ill.

[73] Assignee: Hollister Incorporated, Libertyville, Ill.

[21] Appl. No.: 829,318

[22] Filed: Feb. 14, 1986

Related U.S. Application Data

[63] Continuation of Ser. No. 613,279, May 24, 1984, Pat. No. 4,581,026, which is a continuation-in-part of Ser. No. 521,224, Aug. 9, 1983, abandoned, which is a continuation of Ser. No. 271,086, Jun. 5, 1981, abandoned.

[51] Int. Cl.$^4$ .............................................. A61F 5/458
[52] U.S. Cl. ..................... 604/352; 604/346; 604/347; 604/349; 604/350; 604/351; 604/353
[58] Field of Search ................... 128/760, 767, 138 R, 128/132 R; 604/349, 346, 343, 347, 345, 350, 351, 352, 353; 119/14.42, 14.5

[56] References Cited

U.S. PATENT DOCUMENTS

| 1,423,537 | 7/1922 | Müller | 128/295 |
|---|---|---|---|
| 1,490,793 | 4/1924 | Ajamian | 128/295 |
| 3,353,538 | 11/1967 | Carrigan | 128/295 |
| 3,520,305 | 7/1970 | Davis | 128/295 |
| 3,559,651 | 2/1971 | Moss | 128/295 |
| 3,721,243 | 3/1973 | Hesterman | 128/295 |
| 3,835,857 | 9/1974 | Rogers et al. | 128/295 |
| 3,863,638 | 2/1975 | Rogers et al. | 128/295 |
| 4,187,851 | 2/1980 | Hauser | 128/295 |
| 4,239,044 | 12/1980 | Caulinch | 128/295 |
| 4,270,539 | 6/1981 | Frosch et al. | 604/341 |

FOREIGN PATENT DOCUMENTS

| 2349361 | 4/1975 | Fed. Rep. of Germany | 128/132 R |
|---|---|---|---|
| 162302 | 2/1958 | Sweden . | |
| 217210 | 12/1924 | United Kingdom . | |
| 669063 | 3/1952 | United Kingdom . | |
| 2041753 | 9/1980 | United Kingdom . | |
| 2048680 | 12/1980 | United Kingdom . | |

Primary Examiner—Arthur P. Demers
Attorney, Agent, or Firm—Tilton, Fallon, Lungmus

[57] ABSTRACT

An external catheter, and the methods of making and using such a catheter, for a male urinary incontinence collection system, such system also including an adhesive attachment for holding the catheter in place. The catheter takes the form of a tubular sheath of thin elastic material having a cylindrical body section, a tapered neck section extending from the body section, and a reduced drainage tube section projecting from the neck section. Within the sheath, and constituting a unitary part thereof, is a tubular inner sleeve of soft elastic material having a distal end portion disposed within the neck section and a proximal end portion merging with the sheath's cylindrical body section. The sleeve tapers distally to define an annular space thereabout, and terminates in a reduced distal opening located at an intermediate point within the neck section. The sheath may be produced by a dipping process that includes the preliminary step of stretching a pre-formed tubular member (which ultimately forms the inner sleeve) over a dipping form, followed by successive dipping steps.

4 Claims, 21 Drawing Figures

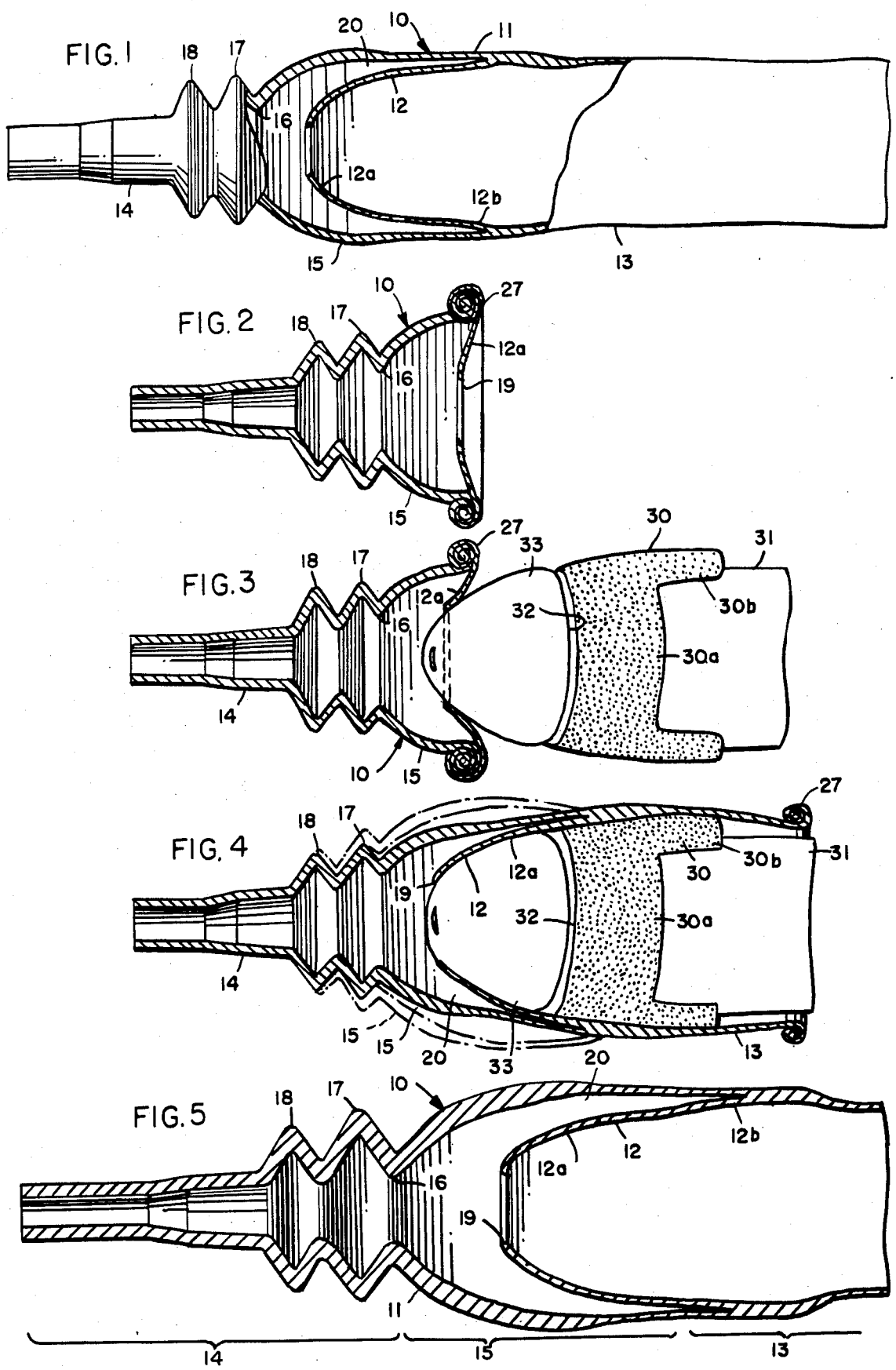

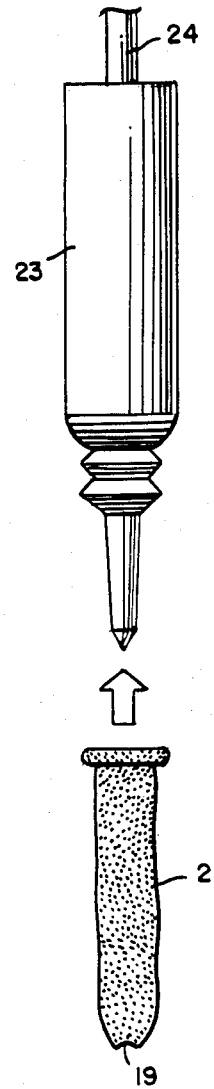
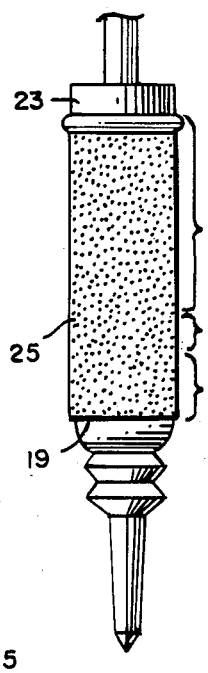
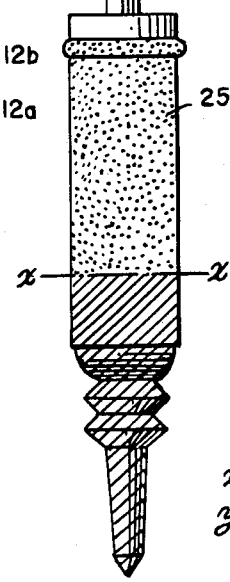
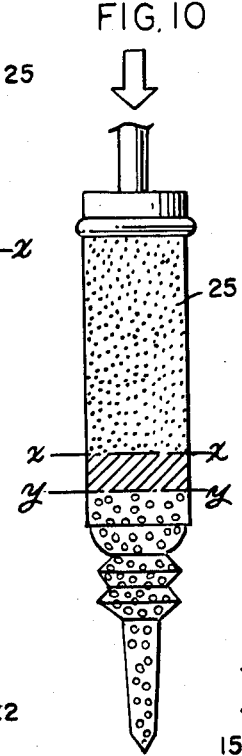
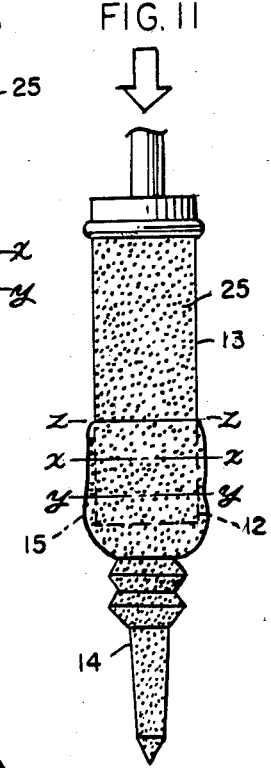
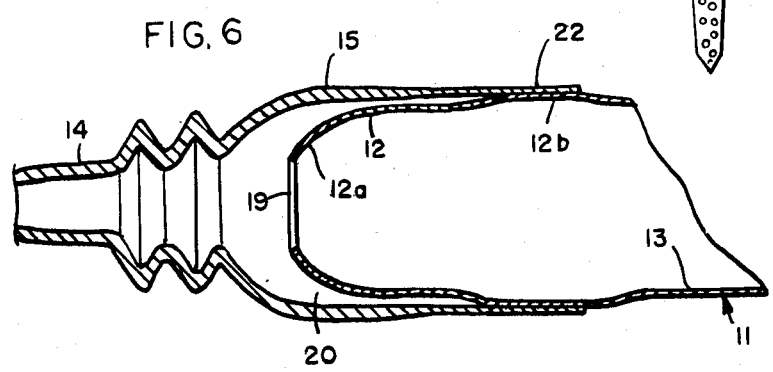

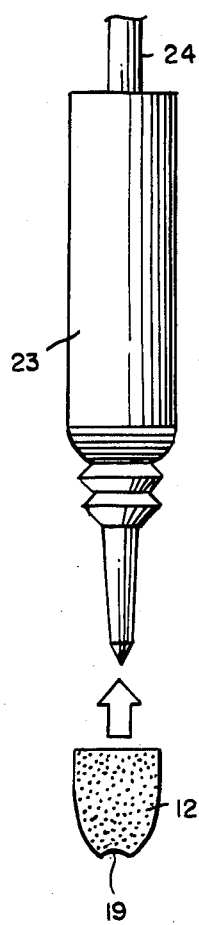
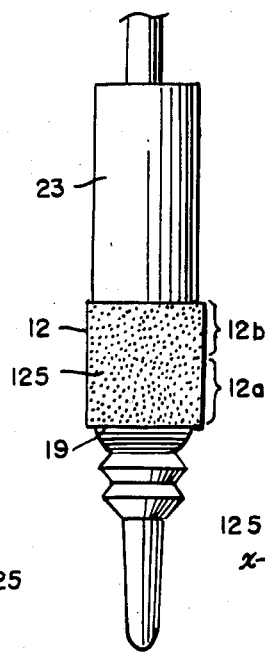
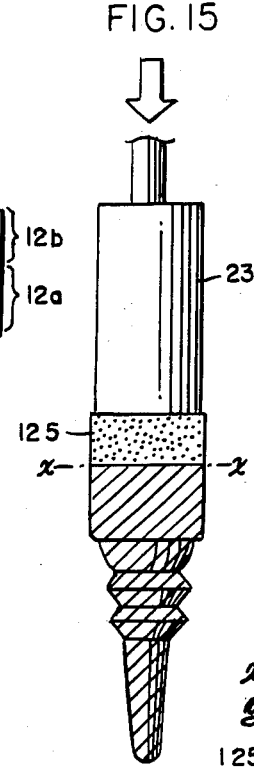
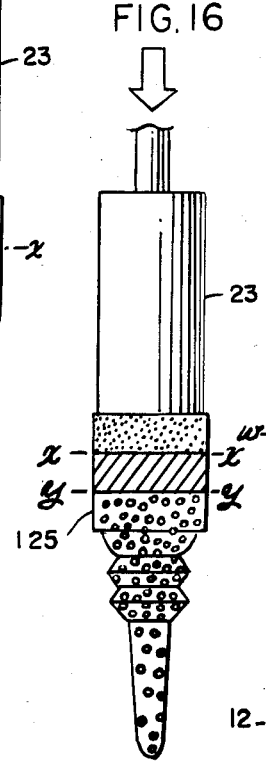
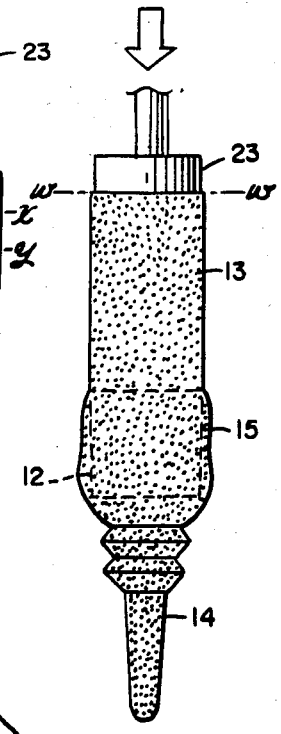
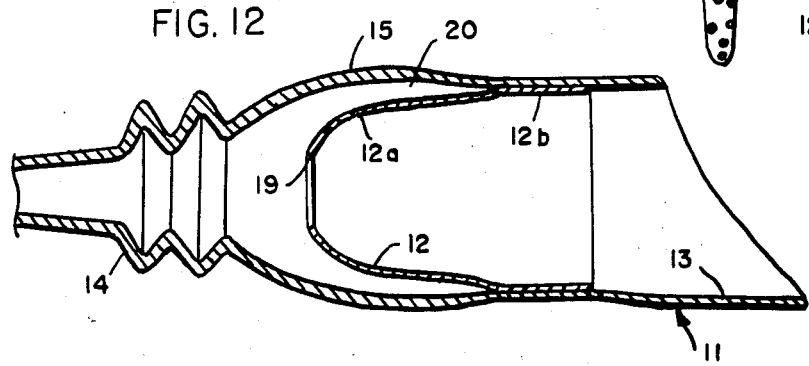

MALE URINARY COLLECTION SYSTEM AND EXTERNAL CATHETER THEREFOR

RELATED APPLICATIONS

This application is a continuation of co-pending application 613,279, filed May 24, 1984, now U.S. Pat. No. 4,581,026, which was a continuation-in-part of application 521,224, filed Aug. 9, 1983 (abandoned), which in turn was a continuation of application 271,086, filed June 5, 1981 (abandoned).

BACKGROUND AND SUMMARY

In co-pending co-owned patent 4,378,018, there is disclosed a male urinary drainage device composed of a thin resilient external catheter and an underlying adhesive sealant pad for holding the catheter in place and for producing an effective seal to prevent urine backup and leakage. The pad is formed of compressible, deformable, water-resistant, and elastic sealant material and includes a ring portion adapted to seal about the penis at or directly behind the glans thereof and a pair of integral strap portions projecting from the ring portion and intended to extend inwardly (proximally) along the penile shaft. The strap portions function primarily to provide catheter retention, whereas the ring portion coacts with the retained catheter and with the penis to serve primarily as a barrier against fluid backup.

The external catheter of U.S. Pat. No. 4,378,018 is provided with convolutions of graduated size in the neck region between the catheter's cylindrical body portion and its reduced drainage tube portion. Such convolutions permit axial as well as radial expansion and contraction and thereby absorb tensioning forces that might otherwise occlude the lumen or reduce effectiveness of the seal between the pad and catheter, or pad and penis, or both. In addition, the convolutions increase the internal capacity of the neck region to accommodate sudden discharges of urine, thereby reducing the possibilities of fluid backup, or disengagement of or damage to the drainage device, under such circumstances.

Conditions may nevertheless arise where a surge of fluid may create a back pressure that may weaken the adhesive seal between the pad and catheter, or between the pad and the penis, resulting in leakage. Should the neck portion of the catheter become enlarged or distorted because of fluid pressure, the forces generated by such pressure will tend to urge the inner surfaces of the catheter laterally out of sealing contact with the annular portion of the pad. Furthermore, apart from the possibility of leakage arising because of surges of fluid causing a failure of the adhesive seal, there is always the risk that gradual deterioration of that seal will occur because of exposure to the urine over an extended period, or that the material of the pad will tend to deteriorate because of continuous exposure to fluid, resulting in undesirable back flow and leakage.

U.S. Pat. No. 2,940,450 discloses a drainage device in the form of an external catheter connected to a flexible tube leading to a suitable receptacle, the catheter being held in place by drawstrings which may be tied together to produce a secure fit. In U.S. Pat. No. 3,835,857, elastic adhesive tape is wrapped about the catheter in place of drawstrings, and in U.S. Pat. No. 3,863,638 a liner is disposed between the catheter to reduce leakage and promote patient comfort. U.S. Pat. No. 4,187,851 discloses a method of forming such a liner in place by wrapping the penile shaft with a double-faced adhesive strip prior to application of the elastic external catheter.

Those devices that have the advantage of being easily and quickly applied tend to be less effective in terms of retention and prevention of fluid backup, whereas those that are more satisfactory in the latter respects are often relatively difficult to apply and more likely to cause patient discomfort and urethral constriction. Ease of application and removal are particularly important because an incontinent patient may have other disabilities that make complicated manipulations difficult if not impossible to perform. Other patents reflecting the state of the art are 364,932, 3,721,243, 3,361,857, 3,511,241, 2,891,546, 4,022,213, 3,526,227, 3,353,538, 1,423,537, 1,015,905, 3,604,424, 4,239,044, 1,490,793, 3,559,651, and 3,405,714.

One aspect of this invention lies in the recognition of the problem of maintaining effective adhesive seals under the conditions described above; a second aspect lies in recognizing that the degradation or rupture of such seals may be prevented by providing the external catheter with an elastic tapered internal sleeve disposed within the neck portion of the outer sheath. In use of the catheter, the sleeve is stretched into sealing engagement with the glans to provide a barrier that tends to prevent liquid from migrating rearwardly or proximally towards the adhesive attachment between the cylindrical portion of the catheter and the penis. Should a surge urine within the neck portion of the catheter cause back pressure, such pressure only tends to increase the effectiveness of the liquid barrier formed between the glans and the sleeve stretched thereabout. Furthermore, when an annular portion of the sleeve is in direct contact with the adhesive pad, as where the sleeve extends slightly behind (proximal to) the corona of the glans, such back pressure increases rather than diminishes the force of adhesive contact with the wearer and thereby promotes an even more effective adhesive seal.

In a preferred embodiment, the adhesive attaching means takes the form of a pressure sensitive adhesive coating along the inner surface of the sheath's cylindrical portion directly behind the sheath's tapered neck section. In some cases the adhesive coating may also be applied to a narrow annular band at the proximal extreme of the sleeve; however, in that event the band should be narrow enough that adhesive contact with the wearer is still limited to an area behind (proximal to) the corona of the glans. Instead of an adhesive coating, the adhesive means may alternatively take the form of a resilient skin-protecting adhesive pad of the type disclosed in aforementioned U.S. Pat. No. 4,378,018, particularly as shown in FIGS. 8–13 thereof. In either case, the adhesive means serves the important function of holding the sheath in position with its stretched inner sleeve retained in protective non-adhesive sealing engagement with the glans. The sleeve includes a proximal end portion, merging and permanently interated with the cylindrical body section of the sheath, and an elongated distal end portion extending and tapering distally into the sheath's neck section. The elongated distal end portion of the sleeve terminates in a reduced opening spaced axially from the distal end of the neck section and has an outer surface unsecured and normally spaced from the neck section along the full length and circumferential extent of the sleeve's distal end portion to provide an expansion space between the sleeve and the neck section. Any increase in pressure within the annular space about the sleeve only tends to urge the sleeve into tighter sealing engagement with the glans. The result is an external catheter which has the advantages of adhesive attachment in terms of patient comfort and convenience, in contrast to prior devices requiring belts, harnesses, and the like, and which at the same time provides a high degree of security against fluid backup and leakage, protects the sensitive dermal surfaces of the glans against direct exposure to urine and the excoriating effects that prolonged fluid contact might otherwise produce, and maintains an effective fluid-tight seal without the discomforts of direct adhesive contact with the glans.

The catheter may be formed in a dipping process that includes the preliminary step of stretching a pre-formed tubular member, ultimately to become the inner sleeve, over a dipping form. In its unstretched or untensioned state, the tubular member has a distal end portion that tapers and terminates in a reduced distal opening. After stretching the tubular member upon the form, the distal end portion of that member is treated to prevent liquid latex from bonding thereto. Thereafter, the form is dipped into a latex bath and the latex coating is then cured to produce the outer sheath, or at least that portion of the outer sheath surrounding the inner sleeve. When the catheter is stripped from the form, the sleeve returns to its original untensioned state, thereby creating an annular space between the outer distal portion of the sleeve and the inner surface of the sheath's neck section.

Other features, objects, and advantages of the invention will become apparent from the drawings and specification.

BRIEF DESCRIPTION OF DRAWINGS

FIG. 1 is a side elevational view, shown partly in section, of an external catheter embodying the present invention, the sheath of the catheter being depicted in unfolded or unrolled condition.

FIG. 2 is a view similar to FIG. 1 but showing the sheath in rolled condition as it would appear prior to application.

FIGS. 3 and 4 illustrate the steps of placing the catheter over a penis upon which an adhesive and protective sealing pad has been fitted.

FIG. 5 is an enlarged fragmentary generalized sectional view of a catheter showing the relationship between the inner sleeve and sheath.

FIG. 6 is a fragmentary sectional view illustrating the relationship between sheath and sleeve in one embodiment of the catheter, and FIGS. 7-11 illustrates the sequence of steps for forming a catheter having such a relationship of elements.

FIG. 12 is a fragmentary sectional view depicting a second embodiment, and FIGS. 13-17 show the method steps for forming a catheter having the relationship of elements represented by the second embodiment.

DETAILED DESCRIPTION OF PREFERRED EMBODIMENTS

Figure 18:
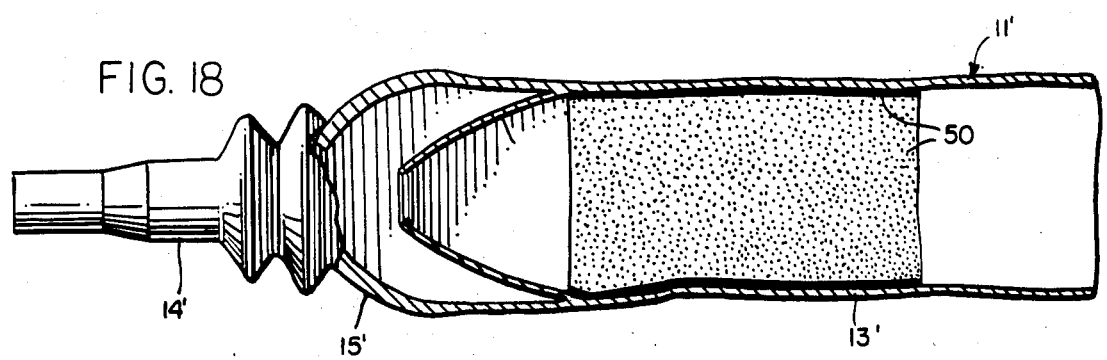
FIG. 18 is an elevational view shown partly in section of a third embodiment.

Referring to the drawings, the numeral 10 generally designates an external catheter formed of soft, highly elastic, natural or synthetic rubber. Natural latex is preferred but other elastomers having similar properties may be used. The catheter includes an elongated outer sheath 11 and an inner sleeve 12, the two being integrated or permanently joined in the manner hereinafter described.

Referring to FIG. 1, the sheath 11 includes an elongated cylindrical section 13, a reduced drainage tube section 14, and a tapered neck section is disposed therebetween. The wall thickness of the cylindrical section 13 is substantially less than that of the neck and drainage tube sections. For example, the cylindrical section may have a wall thickness within the general range of 0.006 to 0.010 inches and, in general, is too thin or limp to retain a cylindrical configuration without support. In contrast, the wall thicknesses of the drainage tube and neck sections may be 0.050 inches or more and are generally great enough so that such sections will retain the configurations shown in the absence of distorting forces and will spring back into the illustrated shapes when distorting forces are removed.

At its forward or distal end, neck section 15 is provided with a rounded taper leading to a reduced opening 16. The drainage tube section 14 that merges with the tapered neck section 15 is provided with a plurality of convolutions or annular enlargements 17 and 18. Two such convolutions of graduated size are depicted, their purpose being to permit greater stretchability, bending, and twisting of the drainage tube section when the device is in use, and to do so with less chance that kinking or obstruction of the lumen might occur. Also, since the interior of the drainage tube section is enlarged at such convolutions, the convolutions increase the fluid capacity of that section and provide a reservoir for accommodating surges of fluid when the device is in use.

The inner sleeve 12 has a distal end portion 12a disposed within the neck section of the sheath and a proximal end portion 12b within the sheath's cylindrical body section. The relationship is depicted most clearly in the generalized and enlarged view of FIG. 5 where it will be seen that the proximal end portion has about the same cross sectional dimensions as the cylindrical body section and merges smoothly with that section, while the distal portion 12a tapers forwardly and inwardly, terminating in a reduced distal opening 19. Opening 19 is spaced well behind (i.e., proximal to) opening 16 at the distal end of neck section 15. The setback also results in the provision of an annular space 20 between the outer surface of the sleeve's distal end portion 12a and the inner surface of neck section 15. The wall thickness of the sleeve 12 may be varied but, to insure conformability, good sealing properties, and wearer comfort, such thickness should approximate that of the relatively thin cylindrical body section 13 of the sheath. Thus, both the cylindrical body section 13 and the inner sleeve 12 should appear as thin, limp, highly stretchable membranes, in contrast to the drainage tube and neck sections 14, 15 with their shape-retaining properties.

In FIGS. 1 and 5 the sheath 11 and inner sleeve 12 are shown as merging smoothly with one another. Although the sheath and sleeve are indeed permanently integrated, and are formed of essentially the same material, they may be formed separately to facilitate production and to achieve the desired setback of the sleeve within the neck section of the sheath. FIG. 6 illustrates a construction wherein the sleeve 12 is actually a continuation of the cylindrical body section of the sheath. The neck section 15 is permanently joined to the body section 13 at 22. Such a construction may be made in accordance with the steps depicted in FIGS. 7–11.

FIG. 7 shows a dipping form 23 having a support shaft 24 that may be mounted upon any suitable reciprocable mechanism (not shown) for dipping the form into a suitable bath of liquid latex. Prior to any dipping operations, an open-ended latex tubular member 25 is stretched upon the cylindrical portion of the form (FIG. 8). Such a fitting and stretching operation may be most readily performed starting with the tubular member 25 in fully rolled condition. The rolled annulus is then simply slipped upwardly onto the lower end of the form 23, is advanced until the reduced opening 19 at the member's lower end is stretched to receive the lower end of the cylindrical portion of the form, and the annulus is then unrolled. Except for the provision of opening 19 at its lower end, tubular member 25 is generally similar to a conventional latex condom.

While some stretching of the upper portion of member 25 necessarily occurs as that member is fitted upon form 23, the greater stretching occurs at the lower portion of that member because in its relaxed state such lower portion is provided with a rounded taper leading to opening 19 (FIG. 7). It is the stretched lower portion of the tubular member that will ultimately become the elongated distal portion 12a of the sleeve of the finished catheter (FIG. 8). The upper portion, subjected to only minimal stretching, is to become the cylindrical section 13 of the sheath.

The form 23 with the elastic tubular member stretched thereon is then subjected to successive dipping steps to produce the neck section and drainage tube section of the final catheter. FIG. 9 indicates that the form is first dipped to a level x—x in a solution or suspension of a suitable release agent that will prevent latex solution from adhering to the treated surface. An alcohol suspension of diatomaceous earth marketed under the designation Snow Floss by Johns-Mansville Corporation, New York, N.Y., has been found particularly effective, but other release agents having similar properties may be used. Thereafter, the form is dipped into an aqueous slurry of calcium nitrate or other suitable activator capable of causing thickening of the latex layer to be subsequently formed by a dipping process, all as well known in the art, and diatomaceous earth. It will be observed that the level y—y to which the form is dipped into the activator slurry is spaced below the level x—x of the release agent treatment (FIG. 10).

After removal of the form from the activator slurry, the coating is allowed to air dry for a short interval (1 to 3 minutes), and the form is then lowered slowly into a latex bath to a level z—z spaced above x—x as indicated in FIG. 11. The form should remain within the bath for an interval within the range of about 4 to 5 minutes; thereafter, the form is removed, dipped in and out of a coagulant solution of calcium nitrate in alcohol. One or more additional dippings into the latex solution, followed by exposure to coagulant, may be undertaken to develop the desired wall thickness. Thereafter, the form or mandrel with the dip coating thereon is placed in an oven at approximately 135° F. for 40 minutes to cure the latex. The form and nearly completed catheter retained thereon are introduced into a water bath maintained at approximately 160° F. for an interval of 30 minutes or more to leach impurities therefrom. Following the leaching step, the catheter is stripped from the form or mandrel, treated with talc to prevent the latex from sticking to itself, and dried. The catheter is completed by cutting away the tip to form the opening at the distal end of the drainage tube section. The end result is a catheter as generally depicted in FIGS. 1 and 5 but in which the layers are formed or joined in the manner specifically illustrated in FIG. 6.

Effective bonding between the two layers of latex may be enhanced by the use of solvents or adhesives applied to the annular zone of the tubular member 25 between lines x—x and y—y. It has been found, however, that an effective bond sufficient to permanently integrate the two layers may be simply achieved by dipping the tubular member into a bath of the coagulant described above following the step of fitting the member 25 upon mandrel 23 (FIG. 8) and before the step of dipping the form into the release agent (FIG. 9). The coagulant coating should be air dried for a short interval (approximately one minute) prior to the dipping step of FIG. 9.

The external catheter of FIGS. 1 and 5 may also be made in accordance with the method steps depicted in FIGS. 13–17 to produce a construction having the particular arrangement of layers shown in FIG. 12. In that embodiment, the inner sleeve 12 is formed from the pre-formed tubular member 125 stretched upon the form or mandrel 23, and the cylindrical section 13, neck section 15, and drainage tube section 14 are then formed by a dipping process and are thus integrated with the tubular sleeve. The procedural steps are similar to those described in connection with FIGS. 7–11 except that the tubular member 125 is relatively short and the cylindrical section 13 of the sheath is formed during the dipping process rather than being provided as an extension of the pre-formed tubular member.

Specifically, the open-ended latex tubular member 125, having a tapered lower end with a reduced opening 19, is stretched over form 23 into the position depicted in FIG. 14. The form is dipped into a coagulant bath and, following an air-drying interval of approximately one minute, is then dipped into a solution or suspension of the release coating material to a level x—x represented in FIG. 15. The form is then dipped into the activator bath of calcium nitrate solution to level y—y (FIG. 16) and, after an air-drying period of approximately 2 minutes, is successively dipped into latex and coagulant baths. The latex-dipping steps are essentially the same as previously described except that the form is lowered into the latex and coagulant baths to a level w—w near the upper end of the cylindrical body of the form or mandrel 23 (FIG. 17). The leaching, stripping, and trimming steps are the same as previously described.

It is to be noted that in both methods the tapered portion of the tubular member 25 or 125 is pre-formed and stretched upon the mandrel. In both instances, when the dipping processes are completed and the catheters are stripped from the mandrels, the stretched inner sleeves 12 are free to contract and thereby produce the setback depicted in FIGS. 1, 5, 6, and 12. Specifically, the released distal portions of the sleeves retract axially and proximally to produce the axial spacing between sleeve opening 19 and sheath opening 16, and also retract inwardly to form the annular spacing 20 (FIG. 5).

The catheter would be rolled prior to use, and would normally be marketed in the rolled condition depicted in FIG. 2. It will be observed that the annular roll 27 is of double thickness, being formed of both the cylindrical body section 13 of the sheath and also a substantial length of sleeve portion 12. The reduced opening 19 at the distal end of the sleeve, as well as the material of the sleeve immediately surrounding that opening, are therefore fully exposed at the mouth of the rolled catheter.

In use of the external catheter, a patient first applies an adhesive pad 30 to the penis 31 as generally illustrated in FIG. 3. The particular pad shown in the drawings is the pad disclosed in the aforementioned U.S. Pat. No. 4,378,018; however, it is to be understood that while such a pad is particularly suitable, other types of adhesive pads may be used. The pad might, for example, be a spiral wrapping of adhesive material as disclosed in U.S. Pat. No. 4,187,851 and in other prior art. The particular pad shown in FIG. 3 is preferred because the ring portion 30a disposed behind the corona 32 of glans 33 provides a smooth annular surface for sealing contact with the catheter, thereby preventing fluid backup and leakage, while the rearwardly (proximally) extending strap portions 30b act primarily as retaining elements for adhesively holding the sheath in place, thereby preventing disruption of the fluid-tight seal in the annular zone behind the corona and particularly the non-adhesive fluid-tight seal formed by the sleeve 12 stretched about the glans. The pad may be formed of any suitable resilient material which is not only deformable but also compressible and at least somewhat elastically recoverable. To obtain these properties, the sealant pad may be prepared from a composition composed principally of an elastomeric material such as synthetic or natural rubber. One such material is described in U.S. Pat. No. 2,570,182, being composed of a blend of nitro rubber and polyvinyl chloride. A material of this kind has been sold under the name "Ensolite", by Uniroyal, Inc. Its use in a sheet arrangement for a male urinary drainage device is described in U.S. Pat. No. 4,187,851. Another such material is composed principally of polyacrylamide and glycerine. This material has been used in ostomy rings and blankets, and has been sold under the name "Crixiline" by Danal Laboratories, Inc., St. Louis, Mo. Other suitable materials can be formulated from gelled mixtures of hydrocolloids such as karaya or carboxymethyl cellulose and polyhydroxy alcohols such as glycerin or propylene glycol, which preferably includes a few percent of fumed silica, as described in co-pending application Ser. No. 383,523, filed June 1, 1982 for "Protective Sealing Composition in Molded Form for Application to the Skin," and prior related applications identified therein, all having a common assignee with the present application. Also, to further improve the desired properties of such compositions for use in the present invention, a minor proportion of polyacrylamide resin can be incorporated, and cross-linked by gamma irradiation. See U.S. Pat. Nos. 4,115,339 and 4,258,715.

The catheter is unrolled over the penis in the manner shown in FIGS. 3 and 4. Specifically, the rolled catheter is positioned with the exposed apertured portion of sleeve 12 in contact with glans 33, and the catheter is then unrolled to allow the sleeve to retract into snug contact with the glans.

Since the distal portion 12a of the sleeve is under slight tension when the external catheter is properly fitted upon the wearer, most of the surface area of the glans, and the areas of the penile shaft and the adhesive pad 30 proximal to the glans, are protected by the sleeve against direct liquid contact. Should there be a surge in the discharge of urine, an uncontrollable occurrence not infrequently associated with spinal injuries, substantial space is provided within the neck section 15 and the convoluted portion of the drainage tube section to aommodate that surge. Ballooning of the sheath and the development of back pressure may nevertheless occur, as indicated in broken lines in FIG. 4. However, should such back pressure develop, such pressure would have the effect of urging the distal end portion 12a of the sleeve into even tighter contact with glans 33, thereby reducing the possibility of leakage. Furthermore, any such back pressure applied to the sleeve 12 in the vicinity of adhesive pad 30 will tend to increase the force of contact between the sleeve and pad and further reduce the possibility of leakage. The result is that the external catheter 10, when used in combination with a suitable adhesive sealing pad, is highly effective in avoiding problems of leakage should sudden surges of fluid, accompanied by the development of back pressure, take place.

It is believed apparent that the external catheter also operates to protect the adhesive seals between pad 30, catheter 10, and penis 31 against exposure to liquid under normal conditions of use, thereby resulting in a combination which should be expected to give the wearer greater security against leakage for longer wearing intervals. Minimizing deterioration of the pad and its sealing properties, as well as the greater comfort arising from reduced continuous exposure of the glans and shaft to the back flow of urine, are significant advantages of this construction.

A suitable composition for use in preparing the sealant pads 30 comprises a mixture of hydrocolloid, polyhydroxy alcohol, fumed silica, and polyacrylamide. A general formula for this type of composition is set out below.

| General Formula | |
|---|---|
| Ingredients | Parts by Weight |
| Hydrocolloid | 15–25 |
| Polyhydroxy alcohol | 50–70 |
| Fumed silica | 1–3 |
| Polyacrylamide resin | 5–20 |

In the above formula, the hydrocolloid may be karaya gum or other natural hydrocolloid such as gelatin, pectin, etc., or a synthetic gum such as carboxymethyl cellulose or hydroxyethyl cellulose, or mixtures thereof. The polyhydroxy alcohol is preferably glycerin, or mixtures of glycerin and propylene glycol, but other polyhydroxy alcohols can be used. An example of suitable fumed silicas are the Cab-O-Sil products of Cabot Corporation, Boston, Mass. The polyacrylamide resin may be a "Reten" resin of Hercules, Incorporated, as described in U.S. Pat. Nos. 4,115,339 and 4,258,271. The cited patents also describe gamma irradiation cross-linking of the polyacrylamide resins, which is a desirable procedure in preparing the material for the sealant pads of the present invention. An example of a presently preferred specific formulation is as follows:

| Specific Formula | |
| --- | --- |
| Ingredients | Weight % |
| Karaya powder | 15.00 |
| Sodium carboxyethyl cellulose | 5.00 |
| Polyacrylamide (non-ionic) | 10.00 |
| Polyvinyl alcohol | 5.00 |
| Fumed silica | 2.00 |
| Glycerin | 59.73 |
| Propylene glycol | 3.05 |
| Methylparaben | 0.09 |
| Propylparaben | 0.02 |
| Butylparaben | 0.11 |
| | 100.00% |

In compounding the foregoing ingredients, a mixture can first be prepared of the liquid ingredients (glycerin, propylene glycol, and the parabens). Fumed silica is then dispersed in the liquid mixture, and thereafter the other powder ingredients are added (karaya, carboxymethyl cellulose, polyacrylamide, and polyvinyl alcohol). The completed mixture is then molded to form the pads, or formed into sheets for use in preparing the pads. Either in pad or sheet form, the material is preferably subjected to gamma irradiation, preferably from a Cobalt-60 radiation source. The amount of radiation employed should be sufficient to sterilize the material, and to achieve cross-linking of the polyacrylamide resin. For example, a radiation level of 2.5 megarads is satisfactory. To increase tackiness, the final product is then coated with a conventional medical-grade vinyl acrylic pressure sensitive adhesive.

Figure 19:
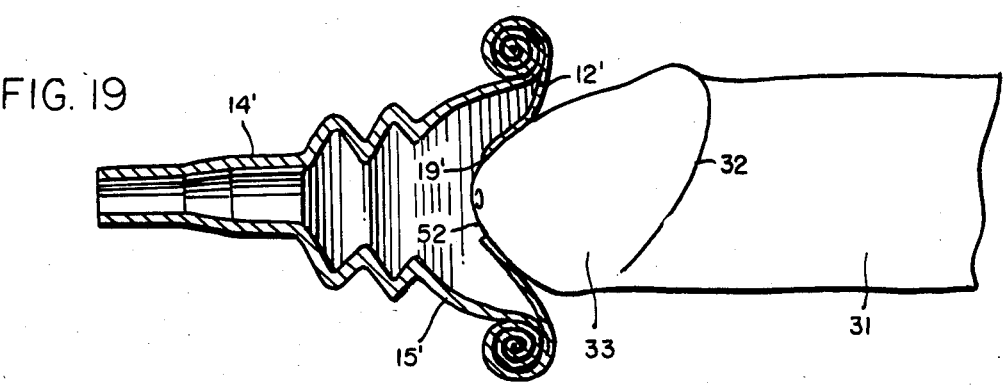
FIG. 19 illustrates the step of placing the catheter of the third embodiment upon the penis.
Figure 20:
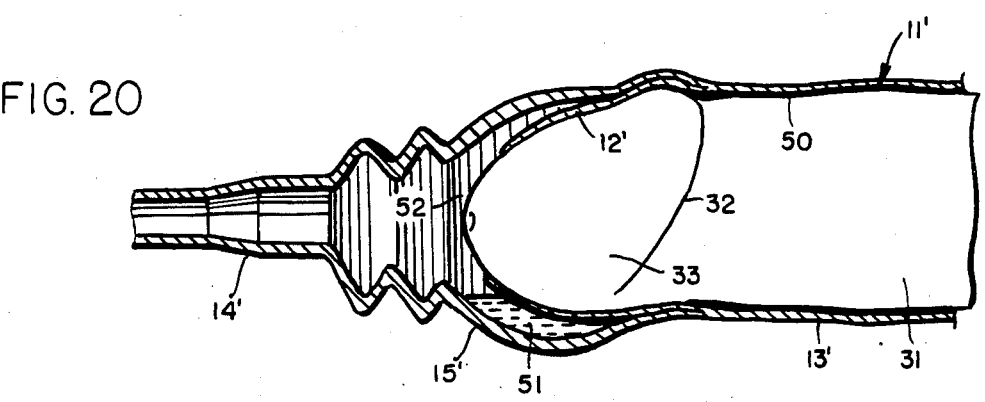
FIG. 20 is a fragmentary sectional view showing the sheath of the third embodiment fitted upon by the penis and also showing the protective effect of the inner sleeve in shielding the glans against liquid contact.
Figure 21:
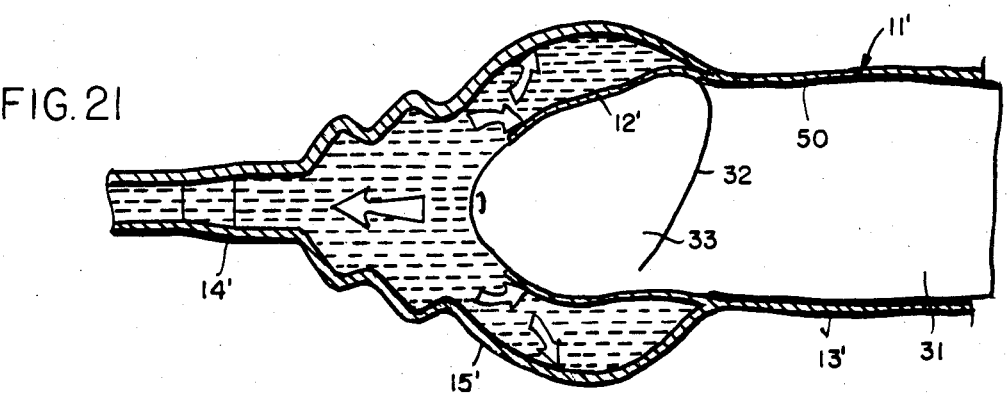
FIG. 21 is a sectional view similar to FIG. 20 but showing, in somewhat exaggerated form for illustrative purposes, the sheath of the third embodiment as a surge of urine suddenly expands the sheath's stretchable neck section.

FIGS. 18-21 illustrate an embodiment of the invention which differs from the arrangement of FIGS. 1-5 primarily because the adhesive attachment means takes the form of an adhesive inner coating or layer 50 within the cylindrical section 13' of sheath 11' rather than as a separate adhesive pad 30. The adhesive coating 50 extends proximally from the proximal end of sleeve 12' and is intended to secure the cylindrical section 13' to the shaft of the penis directly behind corona 32. In the illustration given, the coating extends a major portion of the axial length of cylindrical section 11'; however, the coating may have an axial dimension greater or less than that shown. The primary function of the adhesive coating is to secure the cylindrical section 13' to the shaft of the penis behind corona 32 of glans 33 as shown in FIG. 20, thereby functioning as retaining means to maintain the stretched sleeve 12' of the device in protective non-adhesive sealing engagement with glans 33. Because the sleeve is in stretched condition, the sleeve exerts a force tending to urge the entire sheath in a distal direction, and that force is increased when a surge of urine expands the neck section 15 and tends to displace that neck section distally. Such forces are resisted by the adhesive means 50, thereby maintaining the stretched sleeve 12' in contact with the glans. It is important that such retention is achieved without tenacious (and possibly injurious) adhesive contact with the sensitive dermal surfaces of the glans.

In use, the drainage tube section 14' would be connected to a suitable drainage tube (not shown) as previously described. Upon urination, fluid flows from the neck section and drainage tube section to a suitable collector. However, a small residual amount of urine frequently remains within the neck section 15' as represented by numeral 51 in FIG. 20. In the absence of sleeve 12', such residual urine would remain in contact with the glans and could have an injurious excoriating effect on the delicate tissues of the glans near the corona.

Therefore, unlike other external catheters, the catheters of this invention are provided with an inner sleeve 12, 12' that in normal use is stretched about the glans 33, or at least the proximal portion of the glans near the corona, to protect the glans and at the same time prevent leakage of fluid in a proximal direction beyond the sleeve. The adhesive means 30, 50 holds the stretched sleeve in operative condition and also provides a secondary seal to prevent fluid backup. Should a surge of urine cause ballooning of the neck section 15, 15', as indicated in FIG. 4 (broken lines) and FIG. 21, the effect is to force the stretched sleeve into even tighter sealing contact with the glans 33.

The adhesive coating or band 50 may be any suitable medical-grade pressure sensitive adhesive of the type commonly used for medical tapes and other products. An acrylate ester copolymer adhesive as commonly used for adhesive bandages is effective, and other adhesives having similar properties are also well known and may be used. Ideally, the product is supplied to the user in rolled form as depicted in FIG. 19, thereby simplifying application of the sheath and helping to insure that the adhesive coating 50 will be directed into contact only with the less sensitive skin along the shaft of the penis behind the corona of the glans. To prevent the pressure sensitive adhesive from sticking to the outer surface of the sheath when it is to be unrolled, the outer surface may be coated with any suitable elastomeric release agent to which the adhesive has less affinity. A silicone rubber coating along the outer surface of the sheath is effective for that purpose, but other coating materials capable of producing similar results, as well known in the adhesive tape industry (where such tapes are commonly supplied in rolled form and where the adhesive must release from the outer surface of the tape as it is unrolled) may be used. Alternatively, an interliner of the type also commonly used in the tape industry may be interposed between the adhesive coating 50 and the outer surface of the sheath, such releasable interliner being stripped away by the user to expose the adhesive as the sheath is unrolled.

Assuming that the external catheter is supplied to the user in rolled form, the catheter is first positioned as shown in FIG. 19 with the glans of the penis inserted slightly into the opening 19' of sleeve 12'. As the sheath is unrolled, the stretched sleeve 12' is drawn over the major area of the glans directly behind the urethral meatus 52. Finally, the adhesive-coated cylindrical section 13' of the sheath is brought into contact with the shaft of the penis behind corona 32, thereby immobilizing the catheter and maintaining the stretched sleeve 12' in sealing but non-adhesive engagement with the glans.

As indicated, direct tenacious adhesive engagement between the glans and the sleeve is to be avoided and the embodiments of this invention are capable of achieving that objective while at the same time protecting the glans against objectionable liquid contact and securing the catheter in place by adhesive contact elsewhere (behind the coronal ridge). Protection of the proximal surfaces of the glans occurs because the sleeve 12, 12' is stretched about those surfaces, and it is conceivable that such protection might be enhanced if a suitable sealant having little or no adhesive properties were interposed between the sleeve and the glans. A water-insoluble jelly, or any of a variety of sealant compositions commonly used in the ostomy field, and in the medical field generally, might be employed. In any event, such sealant should make no substantial adhesive contact with the glans, it being both a purpose and an advantage of this system to avoid such adhesive contact while at the same time providing a protective sealing covering over the glans.

While in the foregoing, embodiments of the invention have been disclosed in considerable detail, it will be understood by those skilled in the art that many of these details may be varied without departing from the spirit and scope of the invention.

I claim:

1. A method of securing an external male catheter upon a wearer to protect surfaces of the glans against injury from direct urine contact while at the same time avoiding objectionable adhesive engagement between the catheter and the glans, comprising the steps of providing an external catheter having a tubular sheath formed of soft elastic material and including a thin-walled cylindrical body section, a reduced drainage tube section, a tapered neck section disposed between said body and drainge tube sections, and an inner sleeve of soft elastic disposed within said sheath and having a proximal end portion merging and permanently integrated with said cylindrical section and an elongated distal end portion extending and tapering distally into said neck section; said elongated distal end portion of said sleeve terminating distally in a reduced opening spaced axially from the distal end of said neck section and having an outer surface unsecured and normally spaced inwardly from said neck section along substantially the full length and circumferential extent of said distal end portion; fitting said catheter upon a wearer's penis with said cylindrical section extending along the shaft of the penis behind the glans thereof and with said inner sleve stretched about the glans and in protective but substantially non-adhesive engagement therewith; and maintaining said inner sleeve in protective substantially non-adhesive engagement with said glans by adhesively securing said cylindrical body section to the shaft of the penis behind the corona of the glans.

2. The method of claim 1 in which said step of adhesively securing said cylindrical body section of said sheath to the shaft of the penis comprises first coating at least a portion of the interior surface of said cylindrical body section with a pressure-sensitive adhesive before fitting said catheter upon the wearer.

3. The method of claim 1 in which said step of adhesively securing said cylindrical bdy section of said sheath to the shaft of the penis comprises placing an adhesive pad having tacky adhesive inner and outer surfaces about the penile shaft directly behind the glans prior to the step of fitting said catheter upon the wearer.

4. The method of claim 1 in which said catheter is provided with said cylindrical body section and the proximal portion of said sleeve in rolled form to expose the distal portion of said sleeve in stretched condition within said neck section; said catheter being fitted upon the wearer by first urging the glans into contact with the stretched sleeve of the rolled catheter and with the urethral meatus aligned with the distal opening of said sleeve, and then unrolling said catheter to cover the remainder of said glans with said sleeve and to unroll said cylindrical body section over the penile shaft behind said glans.

* * * * *